(12) United States Patent
Kuhrts

(10) Patent No.: US 6,689,388 B2
(45) Date of Patent: Feb. 10, 2004

(54) MICROENCAPSULATED DELIVERY SYSTEM FOR HIGH VISCOSITY FLUIDS

(75) Inventor: Eric Hauser Kuhrts, Bodega, CA (US)

(73) Assignee: Lipoprotein Technologies, Inc., Bodega, CA (US)

( * ) Notice: Subject to any disclaimer, the term of this patent is extended or adjusted under 35 U.S.C. 154(b) by 106 days.

(21) Appl. No.: 10/000,517

(22) Filed: Oct. 30, 2001

(65) Prior Publication Data

US 2002/0086062 A1 Jul. 4, 2002

Related U.S. Application Data

(63) Continuation-in-part of application No. 09/495,556, filed on Feb. 1, 2000.

(51) Int. Cl.[7] .............................. A61K 9/16; A61K 9/50
(52) U.S. Cl. ...................... 424/490; 424/491; 424/493; 424/496; 424/489; 424/484; 424/485; 424/488; 424/500; 424/501; 424/502
(58) Field of Search .................................. 424/484, 485, 424/486, 489, 499, 500, 501, 502, 490, 491, 493, 496

(56) References Cited

U.S. PATENT DOCUMENTS 6,048,562 A * 4/2000 Mandralis et al. .......... 426/573
6,350,785 B2 * 2/2002 Gehlsen ...................... 514/725

* cited by examiner

Primary Examiner—Thurman K. Page
Assistant Examiner—Liliana Di Nola-Baron
(74) Attorney, Agent, or Firm—Thorpe North & Western, LLP

(57) ABSTRACT

Disclosed is a process for producing powders from high viscosity fluids including mixing a mixture comprising a high viscosity fluid and at least one absorbing agent until a dry dispersion is produced; combining, under shear, a combination of the dry dispersion with a naturally derived oil having a melting point at least about 110° F.; and granulating the combination into a powder. Also disclosed are pharmaceutical compositions that include a high viscosity fluid, at least one absorbing agent; and a naturally derived oil with a melting point at least about 110° F., together with sustained-release embodiments of such compositions.

14 Claims, No Drawings

MICROENCAPSULATED DELIVERY SYSTEM FOR HIGH VISCOSITY FLUIDS

CROSS-REFERENCE TO RELATED APPLICATIONS

This is a continuation in part of Ser. No. 09/495,556, filed Feb. 1, 2000.

FIELD OF THE INVENTION

This invention relates to sustained-release powders made from high viscosity liquids.

BACKGROUND OF THE INVENTION

Many high viscosity fluids have useful utilitarian properties, but need to be converted into a powder so that they can then be employed in various applications. A powder, preferably a free flowing powder, can be weighed more precisely, and can be used in various machinery without clogging the apparatus or plugging various portals. In the pharmaceutical industry, many therapeutic agents are high viscosity fluids, and would need to be converted to a powder to enable a proper dosage form such as a tablet or a capsule. Many food ingredients, nutrients, cosmetics, and feed stuffs are also produced as high viscosity fluids, especially those substances that are in an oil base.

Further, once a high viscosity fluid is converted into a powder, it can then be further processed into a stabilized, sustained-release form. The benefits of producing sustained-release formulations of drugs or other therapeutic agents is now widely recognized in the medical literature and is utilized in many commercial products. It is important to distinguish between solid monolithic dosage forms such as tablets, and powders, and particles that are loosely packed into capsules. A sustained-release powder consists of microparticles that are microencapsulated using a manufacturing process that enables them to be ingested, as, for example a powdered drink-mix which can be added to a liquid and still retain its sustained-release and taste masking properties, or encapsulated in two piece hard shell gelatin capsules. Certain polymer-based microencapsuled powders may behave differently when subjected to the high pressures required to form tablets, and may fracture in the process. In addition, sustained-release tablet formulations may employ other techniques that emanate from their large size, surface area and the swelling properties of hydrocolloids. These are designated monolithic dosage forms, because their sustained-release properties arise from their size. In this case, diffusion and solubility issues become important for sustained-release. It is the rate of diffusion through a thick barrier that produces the sustained-release.

One example of sustained-release dosage forms are multi-particle formulations that when ingested in capsule form, rapidly disintegrate into a large number of subunits. This is fine for drugs that are effective at relatively low doses, or dose levels that can fit into a capsule that is a reasonable size. The amount of drug that can fit into a two piece hard shell capsule that is easy for most people to swallow is at most about 800 mg. based on bulk density of the compound. But when large doses are required, such as for example with nutraceuticals, amino acids, or botanical substances, it is desirable to take them in a powder dosage form that can be mixed with a liquid and consumed.

There are many different ways to microencapsulate drugs that can result in sustained-release properties for the drugs. Many of these methods can be found in M. H. Goucho, *Microcapsules and Microencapsulation Techniques,* 1976, hereby incorporated by reference, M. H. Goucho, *Microcapsules and other Capsules,* 1979, also incorporated by reference; and *Aqueous Polymeric Coatings For Pharmaceutical Dosage Forms,* 1989, (publ. Marcel Dekker, Inc.), further incorporated by reference. Most of the methods of producing sustained-release microparticles can be classified into either physical or chemical systems. Physical methods would include such techniques as pan coating, gravity-flow, centrifuge, and the Wurster Process. The Wurster Process employs a high velocity air stream that is directed through a cylindrical fluidized bed in which the particles are suspended in the air. A coating is sprayed onto the suspended particles, and the particles flow out the top of the cylinder and descend back to the fluidized layer. The flow of air dries the coating, so that successive layers can be applied repeatedly by further spraying. Variables that control the process include the number of cycles, temperature, pressure, and humidity, and can be used to provide the desired coating composition and thickness.

Chemical methods of microencapsulation are usually coacervation or phase separation. This technique involves dissolving a membrane forming polymer in a suitable solvent or vehicle and the drug to be dissolved is suspended in this solution and kept under agitation. The coating precipitates onto a droplet of the drug, similar to crystallization.

Fluidized bed granulation or coating is one of the most common techniques used at the present time for small particle sustained-release. Fluidized bed equipment is available as "top spray", "bottom spray", and "tangential-spray". The core drug is first preheated in the vessel to about 30° C. with hot air, placing the particles in suspension. The floating particles are then sprayed with a polymer to provide a coating, while drying at the same time. Inlet temperature, spray rate, and air throughput must be adjusted to provide optimum end product. Furthermore, the finished particles must be subjected to a post-drying period at around 40° C., where any residual moisture can be driven off. In some case, this last drying period may be up to 24 hours.

Many of the polymers that are used to provide sustained-release properties to powders in the fluidized bed process require solvents such as acetone, isopropyl alcohol, chlorinated solvents, alkanes, methyl ethyl ketone, cyclohexane, toluene, carbon tetrachloride, chloroform, and the like. Evaporation of the solvents becomes an environmental concern, and in many states, it is illegal to release these emissions into the atmosphere. Aqueous or water based polymers are limited mainly to ethyl cellulose and methacrylic acid esters such as poly methacrylate dispersions. In addition, 10–20% of a suitable plasticizer such as triethyl citrate must be added to the polymer. For example, U.S. Pat. No. 5,603,957 uses a solvent-based polymer system to deliver aspirin over a 24-hour period. Preferred solvents are acetone/alkanol mixtures, or cyclohexane, toluene, or carbon tetrachloride. Castor oil, a low melting point oil, is also included in the polymer solvent mix.

Typical aqueous ethyl cellulose polymers currently in wide use include; Surelease®, Colorcon, West Point, Pa., and Aquacoat®, FMC Corporation, Philadelphia, Pa. In the Aquacoat® brochure available on their web site, it is recommended that for sustained-release applications, at least a two hour curing time at 60° C. be conducted to insure reproducible release profiles. This should be done in a tray dryer. Subjecting drugs and other therapeutic compounds such as botanical extracts to 60° C. temperatures for 2 hours or more is likely to result in a loss of potency or degradation of active principles, and is especially problematic for substances with low melting points. Botanical extracts, in particular, have many volatile compounds that can be destroyed if kept at high temperatures for long periods.

Another polymer in common use for sustained-release applications is Eudragit®, Huls America, Somerset N.J. This is a neutral methacrylic acid ester with a small proportion of trimethylammonioethyl methacrylate chloride. This polymer is also applied using the fluid bed process, or can be used in a standard wet granulation procedure.

Wet granulation involves mixing the drug or therapeutic agent with water in a conventional high-speed mixer until a pasty mass, and then dried in an oven over 24 hours at 60° C. Wet granulations have the additional draw back in that they can effect the potency of botanical extracts by causing instability, or transformation. In addition, when dried at 60° C., many sensitive active principles are lost.

Spray drying high viscosity fluids on a maltodextrin carrier is the preferred method for converting wet substances to dry powders. This method is less than ideal in that the yields are usually very low, and the high viscosity fluid or paste must usually be diluted with polysorbate 80 or glucose to reduce the viscosity and enable it to be sprayed without clogging the nozzles of the spray apparatus. Spray drying onto a maltodextrin carrier does not result in sustained-release particles, and furthermore, does not protect the degradation of sensitive compounds, and the stability of these powders is limited.

Carnauba wax has also been used to produce sustained-release dosage forms. Usually, at least a 15% level of wax is applied to the drug for the core, followed by a further coat of ethyl cellulose and polyvinylpyrrolidone (PVP) at about 10 to 15% by weight. This results in drug levels in the cores that range from 50 to 70%, with the other 50 to 30% being the wax and polymers. Synthetic waxes are also available such as Syncrowax®, available from Croda Inc., Parsippany, N.J. These triglyceride waxes have properties similar to carnauba wax, and have melting points of 60–75° C.

Another method of producing sustained-release particles is by starting with sugar spheres or nonpareils. The sugar spheres are also processed in a fluid bed granulator, but the drug must be dissolved in a aqueous solution and sprayed onto the sugar spheres, followed by spray coating with polymers that produce sustained-release as previously mentioned. This system results in large particles that are not acceptable in most drink mix applications, and botanical extracts cannot be dissolved enough to use in this system. The therapeutic agent needs to be absorbed into the sugar particle. The smallest starting particle size for non-pareils is about 60 mesh (US standard sieve number). After coating, the particles are often 30 mesh and larger. The large particle size also presents a problem when encapsulating or tableting.

Melt-spinning techniques involve subjecting a therapeutic agent to sustained heat treatment with a melted polymer which is pumped at a constant rate under high pressure through a plate having a number of small holes, referred to as a spinneret. Filaments emerge from the spinneret into air where they are cooled. These filaments are made into sustained-release formulations. In this process, a polymer is melted on a hot grid or by extrusion-type screw, and then passed to a metered pump. U.S. Pat. Nos. 5,445,769 and 5,458,823 describe the use of a type of melt-spinning technique called a liquiflash spheronization or liquiflash microspheres. Temperatures as high as 130–240° C., which is potentially damaging to the therapeutic agent are often required in this process. In addition, the polymers for the final coats are dissolved in solvents such as acetone and sprayed onto the microshperes in a fluidized bed apparatus with a Wurster column.

Low melting point (below 60° F.) vegetable oil, castor oil, baby oil, margarine, cocoa butter, paraffin, and the like have been used in the pharmaceutical industry for a variety of purposes. For example, soft oils are often used for suppositories. These oils cannot be used to provide powders at room temperature.

U.S. Pat. No. 4,855,326 discloses combining sugar with low melting point oils such as vegetable oil, baby oil, margarine, cocoa butter and the like to help over come hydrophobic properties and facilitate dispersion in water. None of the oils are solid at room temperatures.

In another process, ethyl cellulose, polyvidone and a small amount of castor oil are dissolved in acetone and isopropanol and sprayed onto aspirin particles in a fluid bed granulator such as is described in U.S. Pat. No. 5,603,957. In this case the oil is liquid at room temperatures, and is being used as a plasticizer. The polymers are providing the sustained-release properties, not the oil. Castor oil itself cannot be used to form a powder because of its low melting point.

What is needed are methods and compositions that address the problems noted above.

SUMMARY OF THE INVENTION

In an aspect, the invention relates to a process for producing powders from high viscosity fluids comprising a) mixing a mixture comprising a high viscosity fluid and at least one absorbing agent until a dry dispersion is produced; b) combining, under shear, a combination of the dry dispersion with a naturally derived oil having a melting point at least about 110° F.; and c) granulating the combination into a powder.

In another aspect, the invention relates to a pharmaceutical composition comprising a) a high viscosity fluid, b) at least one absorbing agent; and d) a naturally derived oil with a melting point at least about 110° F.

DETAILED DESCRIPTION OF THE INVENTION

The inventor has unexpectedly discovered that it is possible to solve the above mentioned problems by utilizing the methods and compositions as set forth herein. The recited powders or pharmaceutical compositions have great versatility in their application. The recited powders or pharmaceutical compositions can be used for wound management such as by direct application to burns, abrasions, skin diseases or infections and the like. Other uses such as packing agents for nasal wounds or other open wounds are also contemplated. The recited powders or pharmaceutical compositions may be used in tablets capsules, candy bars, as a food additive, and in drink mixes or soup powders. Additionally, antioxidants, preservatives, and essential oils may be microencapsulated into the recited powders or pharmaceutical compositions to add additional desirable smell or flavor characteristics, or to further stabilize compounds subject to oxidation.

The inventive compositions and recited powders comprise useful dosage forms that can be made from the recited powders including, without limitation, oral forms such as tablets, capsules, beads, granules, aggregates, powders, gels, solids, semi-solids, and suspensions; injectable forms; lotions; transdermal delivery systems including dermal patches; implantable forms or devices; aerosols or nasal mists; suppositories; salves; ointments; and cosmetic powders. The inventive compositions and recited powders may be formulated as sustained-release compositions. Inventive sustained-release compositions preferably have release profiles for therapeutic agents ranging from about 1 to about 24 hours, more preferably from about 6 to about 10 hours. Among other factors, selection of the type and amount of the naturally derived oil can vary the release profile of the inventive compositions and recited powders. The inventive compositions and recited powders can be formulated together with other active and inactive ingredients, both immediate and sustained release.

High viscosity fluids are defined as biologically active fluids having a viscosity greater than about 5 centipoise at 65° F. High viscosity fluids useful in the practice of embodiments of the invention comprise oils, oleoresins, botanical extracts, fruit extracts, spices, vitamins, pharmaceuticals, nutriceuticals, cosmetics, foods, food additives, fertilizers, and fungicides. For example, slow release of fertilizers and fungicides in the soil is especially desirable for nitrogen containing formulas. In a powder according to the invention, the nitrogen fertilizer will tend not to leach out of the soil when wet. In particular, this method of production of powders or pharmaceutical compositions is very useful for processing of botanical extracts and other nutriceutical oils or oleoresins. Other high viscosity fluids useful in the practice of the invention include but are not limited to: fish oil; omega 3 fatty acids; conjugated linoleic acid (CLA); docosahexaenoic acid (DHA); eicosapentaenoic acid (EPA); vitamin E; flax seed oil; carotenoids such as beta carotene; tocotrienols; astaxanthin; lutein; lycopene; essential oils; and botanical extracts such as botanical extracts of hops (*Humulus lupulus* L), kava kava, saw palmetto, various fruits, spices such as rosemary, curcumin, and oregeno; and essentially any high viscosity fluid, such as high viscosity fluids produced by supercritical CO2 extraction or other extraction methods. More than one high viscosity fluids, as in combinations or mixtures of high viscosity fluids, may be used in the practice of this invention.

Some high viscosity fluids according to the invention are fish oil and hops (Humulus lupulus) extract. Fish oil is produced as an oily fluid with a characteristic fish like odor. Processing fish oil according to the invention reduces the smell of fish in the resulting powder or pharmaceutical composition and slows the rate of release of the oil in the stomach. Other essential oils such as rosemary oil can be added to during processing to provide smell masking if desired. It has been found that as little as ½ wt % rosemary oil, based on the total weight of the powder, will impart additional desirable olfactory properties to the finished product. Vanilla extract also provides a pleasing overtone. According to the invention, these spices or essential oils can be dispersed in the powder in a uniform way.

Hops, like many other botanical extracts, is extracted as a high viscosity fluid, such as a paste. If extracted by solvent method, a high viscosity fluid is produced which must be dried (the solvent must be evaporated) and placed onto a carrier. Usually this is achieved by evaporation followed by spray drying. If supercritical CO2 extraction is used, the resulting extract is a paste, and while there is no need to evaporate off residue solvent, the thick paste is very difficult to use in solid dosage forms. The method and compositions described herein offer a solution to the end products of botanical extraction, because this high viscosity fluid can be converted to a relatively high yield powder. Furthermore, the attendant microencapsulation during the recited combination helps to slow down degradation of sensitive principles in the extract, or helps to slow down oxidation of oils due to exposure to oxygen, moisture, or light. The resulting end product is therefore further stabilized by the complete process described herein.

Hops (*Humulus lupulus*) may be extracted using a variety of methods, and the resulting high viscosity fluid is standardized and the viscosity adjusted with the addition of glucose. The resulting extract may contain, in certain embodiments, about 42% alpha acids. Hops has been in use by the beer industry for hundreds of years. There are at least six flavonoids that can be isolated from hops, and some of these flavonoids have antiproliferative and cytotoxic effects. Some of the compounds in hops have also been shown to inhibit growth of human breast cancer cells. The unique compounds isolated from hops therefore have potential as cancer chemopreventive agents by effecting the metabolism of carcinogens. Hops also exhibits antimicrobial properties.

Extraction of hops also yields various essential oils, oleoresins, and alpha and beta acids. The primary alpha acids in hops comprise humulone, cohumulone, hulupone, adhumulone, and xanthohumols. The primary beta acids in hops comprise lupulone, colupulone, and adlupulone. Hops resin is obtained from the yellow vesicles in the flowers of the hops plant. Extraction of hops resin is usually done using accepted extraction techniques with such solvents as hexane or ethyl alcohol, which concentrates the alpha and beta acids. Liquid carbon dioxide under super critical conditions, or chromatography can be used to separate the alpha and beta fractions. This usually results in a pasty material, which is then diluted and spray dried on a carrier.

Supercritical fluid technology is a more recent and superior means of extracting and concentrating the active principles that are contained in botanical extracts. Furthermore, supercritical fluid extraction is not a solvent based system, so it results in solvent free extractions, and is less harmful to the environment, because there is no need to evaporate the solvents. CO2 is the most commonly used material in supercritical fluid extraction and fractionation. Supercritical CO2 extraction also allows for better separation and fractionation of certain components in hops that may not be necessary for a particular application, such as the elimination of estrogenic components which may not be needed in an anti-inflammatory formula. Ethanol extracts of hops are known to possess strong estrogenic properties.

The anti-inflammatory properties of hops extract has been traced to one of the bitter principles or resins in hops called humulone. In one study, humulone inhibited arachidonic acid-induced inflammatory ear edema in mice (Yasukawa, K et al, Oncology 1995, March; 52(2): 156–158), and also inhibited skin tumor formation following initiation with a chemical challenge. Humulone, the alpha acid contained in hops, has also been shown to suppress cyclooxygenase-2 induction at the level of transcription (Yamamoto K, et al, FEBS Lett Jan. 14, 2000, 465(2–3: 103–106). Humulone, therefor, could be considered a COX-2 inhibitor. Furthermore, humulone suppressed the TNFalpha-dependent cyclooxygenase-2 induction with an IC(50) of about 30 nM, a fairly low concentration.

While hops extract has many desirable properties, the widespread use of a potent extract such as is produced by supercritical extraction, wherein certain active principles have been concentrated, has been hindered due to its nature as a high viscosity fluid.

Astaxanthin is a fat soluble nutrient, a xanthophyl pigment which is an oxygen derivative of the carotenoid family.

Astaxanthin is a high viscosity fluid useful in the practice of this invention. It is a powerful antioxidant derived from microalgae. Unfortunately, once converted to a dry form, astaxanthin is not very stable. Over a three-month period, dry astaxanthin powder loses about 40% of its potency, giving it a short shelf life. Processing astaxanthin according to the invention can extend its shelf life.

The inventive process is distinguishable from conventional solvent-based systems in that preferably no solvents are driven off or evaporated during the process in order to achieve the recited powder. This is an advantage, for the reasons noted above. Furthermore, the inventive pharmaceutical compositions are preferably free from solvents introduced during the process of producing the pharmaceutical composition (this specifically excludes solvents that might be present in non-solvent raw materials used to manufacture the pharmaceutical composition such as solvents used to extract botanicals).

A naturally derived oil having a melting point at least about 110 degrees F., such as an hydrogenated soy oil, will be substantially solid at room temperatures. Naturally derived oils are defined as oils obtained from an animal or vegetable source. In fact, such a naturally derived oil with a melting point at least about 110 degrees F. will melt only at temperatures that are significantly above those temperatures normally encountered by food or pharmaceutical products, even during shipment on hot days. Accordingly, a process or pharmaceutical composition that comprises a naturally derived oil with a melting point at least about 110 degrees F., but less than about 200 degrees F., will not degrade during normal product shelf conditions and yet will not require exposing a biologically active material in the high viscosity fluid, or elsewhere in the recited powder or pharmaceutical composition, to heat that could degrade the biologically active material during the processing of the recited powder or pharmaceutical composition. Naturally derived oils with a melting point at least about 110° F. are useful in the practice of this invention, preferably with melting points from about 120 to about 200° F., and more preferably from about 120 to about 180° F. These melting points are usually below the melting point of most drugs or therapeutic compounds, and are achievable using equipment described herein or known to one of skill in the art.

Preferred naturally derived oils comprises vegetable oils, such as soy oil. These oils are very acceptable to health conscious consumers, and appear user friendly on the label. A preferable naturally derived oil is an hydrogenated soy or cottonseed oil with a melting point of at least about 140 degrees F. In an embodiment, a naturally derived oil useful in the practice of the invention is Sterotex HM®, manufactured by AC Humko, Memphis Tenn. Sterotex HM® is a spray chilled hydrogenated cottonseed oil that completely melts at least about 150° F. This naturally derived oil is completely solid at lower temperatures, and is available as a powder. Some naturally derived oils are available in flake form such as the hydrogenated soy oil Dritex-S, also from AC Humko. Other naturally derived oils of similar melting points are available, but are usually in a solid mass, and must be chiseled or chipped apart, and therefore are difficult to use and weigh out. Either Sterotex HM® or Dritex-S is preferable, for handling reasons, to solid mass naturally derived oils. Stearic acid is an naturally derived oil that is derived from either animal or vegetable sources and has a melting point of about 140 to about 150° F. The naturally derived oil according to the invention is preferably present in an amount ranging from about 0.5% to about 15% by weight based on the total weight of the powder, more preferably present in an amount ranging from about 0.5% to about 5% by weight based on the total weight of the powder, and most preferably present in an amount ranging from about 1% to about 2% by weight based on the total weight of the powder.

Absorbing agents useful in the practice of this invention comprise carbohydrates, proteinaceous materials, fibers or silica. Preferable carbohydrates comprise maltodextrin, corn starch, corn syrup solids, and glucose. The maltodextrin used herein can be any suitable maltodextrin that will dilute and absorb high viscosity fluids. Maltodextrin may be produced from corn starch and is a complex carbohydrate. Preferable proteinaceous materials comprise sodium casseinate, soy protein, and whey protein. Preferable fibers comprise acacia gum, guar gum, and pectin. The silica preferably is a high porosity spherical silica such as fumed silica with a high oil absorption capacity and small surface area. The preferable average silica particle size distribution is usually about 0.01 to 0.05 microns as determined by electron microscope. The preferable oil absorption of silica materials is about 200–500 ml/100 g, and the preferable bulk specific gravity about 0.1 g/ml or less. In an embodiment, one or more absorbing agents may be combined. For example, in an embodiment, silica and maltodextrin may be combined to improve the absorbance of a high viscosity fluid such as an oil or oleoresin.

Other materials, such as additives may be added to the inventive compositions. Examples of classes of additives include excipients, lubricants, hydrocolloid suspending agents, buffering agents, disintegrating agents, stabilizers, foaming agents, pigments, coloring agents, fillers, bulking agents, sweetening agents, flavoring agents, fragrances, release modifiers, etc. Furthermore, biological active substances, other than those present in the high viscosity fluid, may be included in the inventive compositions and powders. For example, a high viscosity fluid such as hops extract paste may be combined with an non-steroidal anti-inflammatory drug.

A variety of additives can be incorporated into the inventive compositions for their intended functions. These additives are usually used in small amounts. In some cases, additives such as hydrocolloids are used as suspending agents, as for example in a powdered drink mix that is reconstituted in liquid. Anti-oxidants or other preservatives may also be added.

Useful additives include, for example, gelatin, vegetable proteins such as sunflower protein, soybean proteins, cotton seed proteins, peanut proteins, rape seed proteins, blood proteins, egg proteins, acrylated proteins; water-soluble polysaccharides such as alginates, carrageenans, guar gum, agar—agar, gum arabic, and related gums (gum ghatti, gum karaya, gum tragacanth), pectin; water-soluble derivatives of cellulose: alkylcelluloses, hydroxyalkyl celluloses and hydroxyalkylalkyl celluloses, such as methylcellulose, hydroxymethylcellulose, hydroxyethylcellulose, hydroxypropylcellulose, hydroxyethylmethylcellulose, hydroxpropylmethylcellulose, hydroxbutylmethylcellulose, cellulose esters and hydroxyalkylcellulose esters such as: cellulose acetate phthalate (CAP), carboxyalky I celluloses, carboxyalkylalkyl celluloses, carboxyalkyl cellulose esters such as carboxymethyl cellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVP/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylan-finoethyl group, which may be quaternized if desired; and other similar polymers.

Processing aids such as sucrose, polydextrose, maltodextrin, PEG 1500, polysorbate 80, lactose, maltose, vegetable glycerine and the like may also be used. In some cases where accelerated release is desired, a sugar may be incorporated into the hot melt. Since the oil coating is hydrophobic, incorporating a hydrophilic sugar in the hot melt helps counteract the tendency of the particles to float. The sugar also helps to increase the rate of release of the core material by providing solubility to the matrix. Other substances such as calcium carbonate or other minerals can be added to provide weight to the particles and effect the release profile.

Mixing a mixture that comprises a high viscosity fluid and at least one absorbing agent until a dry dispersion is produced may be accomplished using a variety of mixers. This type of mixer can be the same mixer that is used in the granulating step. The apparatus that is used to manufacture the powder may include a Littleford W-10 vertical or horizontal high intensity mixer (LittlefordDay, Florence Ky.), or a standard Hobart type mixer or plow mixer. These mixers are preferably jacketed with a hot water or steam bath such that the ingredients, such as the naturally derived oil may be melted by a combination of the heat produced by the heated vessel and/or the work input from the mixer itself. The heat produced in the jacket may be produced by either steam or hot heat transfer fluid that runs through the jacket. In certain embodiments, the mixer may be fitted with special plows or augers. The unique mixing action of the auger shaft or plows revolving at a high rate of speed causes the mixed ingredients to fluidize in free space, providing a high volume rate of material transfer throughout the entire length of the vessel. In an embodiment, the mixing is accomplished using a high shear/high intensity mixer with a heating jacket and heated spray lines. In another embodiment, the mixing is accomplished using a plow type mixer fitted with a heated jacket, heated tank, and heated spray lines.

The inventive process results in the mixing, blending and melting of the ingredients fairly quickly and in the same process. In addition, the vessel can be fitted with high speed impact choppers to enhance mixing and or drying. The high viscosity fluid is added to the mixer, together with at least one absorbing agent, and the mixture is mixed until a dry dispersion is produced. The relative concentrations of high viscosity fluid and absorbing agent(s) may be varied according to the nature of the high viscosity fluid and absorbing agent(s); preferably the high viscosity fluid ranges from about 25 wt % to about 85 wt % based on the total weight of the mixture. In an embodiment, the mixture may be heated above about 110 degrees F. during the mixing.

To the dry dispersion is then added a naturally derived oil with a melting point at least about 110 degrees F. The temperature of the combination is increased to melt the naturally derived oil while simultaneously mixing with the dry dispersion and any other additives or ingredients present. This combining under shear typically takes up to 20 minutes, although the time will vary from instance to instance and may continue until the dry dispersion is substantially coated with the naturally derived oil. When fully mixed, the combination may be cooled, while continuing to be mixed, until the naturally derived oil solidifies thereby granulating the combination into a powder. A coating is thus provided around the dry dispersion, and in effect, a microencapsulated powder or pharmaceutical composition may be produced. This dry granulated/microencapsulated powder/composition is then suitable for tableting or filling into two-piece hard shell capsules. The resulting powder/composition is also stabilized and may exhibit sustained-release properties when placed into dissolution. In an embodiment, the inventive pharmaceutical compositions are sustained-release pharmaceutical compositions.

If desired, molten naturally derived oil may be sprayed on the dry dispersion from a heating tank fitted with heated insulated lines using a tower-mounted, hydraulic atomizing nozzle. This results in less compaction of the particles because more shear results in harder particles. In some cases this may be desirable for shorter release profiles. Surprisingly, the high shear mixer with good compaction of the dry dispersion can result in sustained-release profiles that span over 24 hours with only a 1–2% by weight oil level. In other words, 98–99% of the powder is the high viscosity fluid. This sustained-release powder is of fine particle size, has better shelf life (stability), and exhibits excellent flow properties, and may be used as a food additive, incorporated into a powdered drink mix, or manufactured into solid dosage forms.

An advantage of the invention is that it provides a sustained-release microencapsulation process that can be inexpensively and quickly produce a powder with a very high percentage of active substance. It is a further advantage of the instant invention not to necessitate the use of solvents or synthetic polymers, although polymers can be used as an additional means of control if desired. It is a further advantage of the present invention not to require extremely high temperatures (i.e. temperatures greater than about 200 deg F.) to produce the powder/composition, and to shorten the length of time the materials are processed or exposed to elevated temperatures or hot air.

It is an additional feature of this invention to produce sustained-release powders from high viscosity fluids that are directly compressable into tablets without fracturing, and with the need for few additional excipients in the tablets. The term coined by the pharmaceutical manufacturing industry for this attribute is "direct compression". A directly compressable powder does not need to be blended with many other excipients in a slurry (wet granulation) and then baked in ovens to dry and crushed into a powder. In this invention, the powders so produced can be directly tableted without wet granulation. Furthermore, the powders described herein still maintain their sustained-release properties after tableting, and do not fracture, due to the soft nature of the microparticles produced by this technique.

In the present invention, the drug particles are processed in a way to yield a high percentage of active component powder that is virtually indistinguishable from the original active component itself. Surprisingly, powders consisting of 50% of the active agent are possible that release over many hours.

EXAMPLES

Example 1

Fish oil is added to a plow mixer, which was capable of operating at high temperatures because it was jacketed with a second layer to allow hot water to flow around the vessel. Silica (5 wt % based on total weight of mixture) and maltodextrin (45 wt % based on total weight of mixture) are added to the fish oil (50 wt % based on total weight of mixture). The fish oil, maltodextrin, and silica are blended as the temperature is slightly elevated. After complete mixing and dispersion, the fish oil is converted into a free flowing, fine dry powder. To this powder is then added hydrogenated soy oil flakes (Dritex S®, AC Humko, Memphis, Tenn.). The hydrogenated oil flakes were added to a 2% weight gain based on the finished weight of the dry dispersion. A high-speed chopper operating at 10 hp was fitted at the discharge point. Efficient coating or microencapsulation of the powder was achieved in about 20 minutes when a temperature of about 155° F. was reached and the hot oil thoroughly mixed with the powder. Cooling was achieved by discharging the batch into a cooler mounted directly below the mixer. The resulting granules were small, free flowing, and exhibited sustained-release properties when a dissolution test was conducted. The weight percent of the fish oil in the finished product was about 50% based on total weight of the powder, and the hydrogenated soy oil was 2 wt % based on total weight of the powder. The resulting fish oil powder had a greatly reduced smell of fish.

Example 2

Fifty wt %, based on total weight of the mixture, conjugated linoleic acid (CLA) oil was charged to a Littleford W-10 high shear mixer with a hot water jacket to allow circulating hot water to keep the vessel hot. Ten wt %, based on mixture total weight, silica and 40 wt %, based on mixture total weight, maltodextrin were added to the vessel and mixed thoroughly until a dry dispersion was produced. After mixing and granulating the various components, absorption of the oil had occurred, resulting in a dry free flowing powder. To this powder was added spray chilled hydrogenated soy oil powder at a 2 wt % level, based on total dry dispersion weight. The mixer work input was increased to 2000 RPM and then adjusted down to about 600 RPM for 5 minutes. The high shear of the mixer and the hot water jacket melted the oil and mixed it with the core ingredients. The powder was discharged into a cooler mounted below the unit. The resulting particles were small, powder like, free flowing, and exhibited surprisingly excellent sustained-release properties as tested according to the dissolution testing protocol indicated below:

Dissolution Testing Protocol

Simulated gastric fluid (SGF) and simulated intestinal fluid (SIF) can be prepared according to USP, or as follows:
1. Alternative preparation of simulated gastric fluid (SGF) (pH 1.2)
    Sodium chloride (2 g) and pepsin (3.2 g) are co-dissolved in 7.0 ml of hydrochloride acid. Deionized water is added to make the final volume equal to 1000 ml. pH should be 1.2. Pepsin activity of 800–2500 units per mg. of protein is available from Sigma. Equilibrate to 37 degrees C.
2. Alternative Preparation of simulated intestinal fluid (SIF) (pH 7.5)
    Monoacid potassium phosphate (23.8 g) is dissolved in 875 ml of water. Sodium hydroxide (665 ml, 0.2N) and 1400 ml of water are then added. Pancreatin (35 g) is added and the resulting solution is adjusted with 0.2N sodium hydroxide to a pH of 7.5+−0.5. The solution is diluted with water to a final volume of 3500 ml. Equilibrate to 37 degrees C.

Use basket method, and set rotation speed at 50 RPM and maintain dissolution media at 37 degrees C.

Sample points:

1 and 2 hours in simulated gastric fluid (SGF), drain and refill with SIF.
3, 5 and 8 hours in simulated intestinal fluid (SIF).
Results

| Sample ID | % Oil released in GI fluids (g/100 g sample) | % Oil remain. in matrix |
|---|---|---|
| SGF 1 hour | | |
| 110 | 0.68 | 45.84 |
| 113 | 0.94 | 45.00 |
| 115 | 1.57 | 47.23 |
| 118 | 2.04 | 46.13 |
| SGF 2 hours | | |
| 210 | 1.44 | 47.46 |
| 213 | 3.35 | 44.82 |
| 215 | 4.25 | 43.67 |
| 218 | 10.45 | 37.33 |
| 218p | 41.15 | 7.72 |
| 10 | 27.99 (without GI fluids treatment) | |

SGF-simulated gastric fluid
SIF-simulated intestinal fluid

Sample ID No. Explanation

110=SGF 1 hour, extracted with petroleum ether
113=SGF 1 hour+SIF 3 hours, extracted with petroleum ether
115=SGF 1 hour+SIF 5 hours, extracted with petroleum ether
118=SGF 1 hour+SIF 8 hours, extracted with petroleum ether
210=SGF 2 hours+SIF 0 hour, extracted with petroleum ether
213=SGF 2 hours+SIF 3 hours, extracted with petroleum ether
215=SGF 2 hours+SIF 5 hours, extracted with petroleum ether
218=SGF 2 hours+SIF 8 hours, extracted with petroleum ether
218p=SGF 2 hours+SIF (with 3 ml of petroleum ether on the top of SIF) 8 hours, extracted with petroleum ether.
10=extracted with petroleum ether at room temperature without GI fluids.

As can be seen from the above dissolution test conducted in simulated physiological fluids, the conjugated linoleic acid was released very slowly form the microencapsulated powder. It is very surprising and unexpected that such a small amount of hydrogenated oil as the coating agent resulted in such a prolonged release profile. At the data point numbered 218p, which was 2 hours in simulated gastric fluid (SGF) followed by 8 hours in simulated intestinal fluid (SIF), and extracted with petroleum ether on top of the SIF, only about 41% of the oil had been released from the powder. Thus, this oil powder probably had a release profile that spanned up to 24 hours.

Example 3

Five kg astaxanthin oleoresin is charged to a Littleford high intensity mixer with maltodextrin and silica sufficient to absorb the oleoresin, and mixed at 1000 RPM until a dry dispersion is formed. Sterotex HM® hydrogenated soy oil is added at a 1 wt % level, based on total weight of the dry dispersion, and the speed of rotation is increased to 2000

RPM and the temperature elevated to melt the hydrogenated oil. The RPMs are then decreased to maintain the power draw to within the allowable motor amperage. After 3–5 minutes the oil is fully melted and mixed with the core materials, and upon inspection, the batch is fully granulated. The temperature of the jacket is lowered and the powder is discharged into the cooling unit and appears as a fine granular, free flowing sustained-release powder. Astaxanthin stability, over the times resported, was measured using HPLC, with the following results:

Accelerated Astaxanthin Stability Data (wt %)

| Baseline: | 3.9%* | Control: | 4.0%* |
|---|---|---|---|
| 14 days: | 4.4 | | 3.6 |
| 28 days: | 4.3 | | 3.2 |
| 42 days: | 4.2 | | 2.6 |
| 56 days: | 4.4 | | 2.4 |
| 84 days: | 4.1 | | 2.38 |

*Amount, by weight, of astaxanthin in the oleoresin extract.

The above data summarizes stability studies that were conducted with astaxanthin oleoresin that had been converted into a dry form and then microencapsulated. The control, which was the dry astaxanthin powder, experienced about 40% degradation whereas the microencapsulated astaxanthin was stabilized, and remained at essentially the same potency at the 84-day time point as the starting point or baseline potency. It was surprising and unexpected that only a 1% coating of oil was sufficient to stabilize astaxanthin in a three-month stability study.

Example 4

Hops extract, at 50 wt % (based on total weight of mixture) is added to a jacketed high intensity mixer with 7 wt % silica and 43 wt % maltodextrin. The mixture temperature is elevated, and mixing continues until powder is produced. The temperature is then lowered, and hydrogenated cottonseed oil with a melting point of about 150 degrees F. is added at a 2% weight gain, based on the weight of the dry dispersion. The temperature of the combination is again elevated to melt the oil, and mixing continued. The temperature is then lowered to room temperature, and the resulting powder discharged. The hops extract composition was a faint green, free flowing, very fine powder that could now be tableted or placed into two piece hard shell capsules.

While the present invention is described above in connection with the preferred or illustrative embodiments, those embodiments are not intended to be exhaustive or limiting of the invention, but rather, the invention is intended to cover any alternatives, modifications or equivalents that may be included within its scope as defined by the appended claims.

What is claimed is:

1. A pharmaceutical composition comprising:
    a) a high viscosity fluid having a viscosity of at least 5 centipoise at 65° F.;
    b) at least one absorbing agent admixed with the high viscosity fluid to form a dry dispersion; and
    c) a naturally derived oil with a melting point at least about 110° F., wherein the dry dispersion is microencapsulated within the naturally derived oil.

2. The pharmaceutical composition of claim 1, wherein the pharmaceutical composition is a sustained-release composition.

3. The pharmaceutical composition of claim 1, wherein the at least one absorbing agent comprises a member selected from the group consisting of: carbohydrates, proteinaceous materials, fibers, and silica.

4. The pharmaceutical composition of claim 3, wherein the carbohydrates comprise a member selected from the group consisting of: maltodextrin, corn starch, corn syrup solids, and glucose.

5. The pharmaceutical composition of claim 3, wherein the proteinaceous materials comprise a member selected from the group consisting of: sodium casseinate, soy protein, and whey protein.

6. The pharmaceutical composition of claim 3, wherein the fibers comprise a member selected from the group consisting of: acacia gum, guar gum, and pectin.

7. The pharmaceutical composition of claim 1, wherein the high viscosity fluid comprises a member selected from the group consisting of: oils, oleoresins, botanical extracts, fruit extracts, spices, vitamins; pharmaceuticals, fungicides, and fertilizers.

8. The pharmaceutical composition of claim 1, wherein the high viscosity fluid comprises a member selected from the group consisting of: oils; oleoresins; botanical extracts; fruit extracts; spices; vitamins; pharmaceuticals; nutriceuticals; cosmetics; foods; food additives; fertilizers; fish oil; omega 3 fatty acids; conjugated linoleic acid; docosahexaenoic acid; eicosapentaenoic acid; vitamin E; flax seed oil; carotenoids; tocotrienols; astaxanthin; lutein; lycopene; essential oils; and mixtures thereof.

9. The pharmaceutical composition of claim 7, wherein the botanical extracts comprise extracts selected from the group consisting of hops, kava kava, saw palmetto, fruits, spices; and mixtures thereof.

10. The pharmaceutical composition of claim 1, wherein the naturally derived oil is a vegetable oil with a melting point between about 120° F. and 200° F.

11. The pharmaceutical composition of claim 1, wherein the naturally derived oil is an hydrogenated soy or cottonseed oil with a melting point of at least about 140° F.

12. The pharmaceutical composition of claim 1, wherein the naturally derived oil comprises from about 0.5% to about 15% by weight, based on the total weight of the composition.

13. The pharmaceutical composition of claim 12, wherein the naturally derived oil comprises from about 0.5% to about 5% by weight, based on the total weight of the composition.

14. The pharmaceutical composition of claim 13, wherein the naturally derived oil comprises from about 1% to about 2% by weight, based on the total weight of the composition.

* * * * *